United States Patent [19]

Voss et al.

[11] Patent Number: 5,731,344
[45] Date of Patent: Mar. 24, 1998

[54] BISHISPIDINE COMPOUNDS, PROCESSES FOR THEIR PRODUCTION AND PHARMACEUTICAL AGENTS CONTAINING THESE COMPOUNDS

[75] Inventors: Edgar Voss, Viernheim; Rudolf Reiter, Wemheim; Claus Kilpert, Mannheim, all of Germany

[73] Assignee: Boehringer Mannheim GmbH, Mannheim, Germany

[21] Appl. No.: 615,248

[22] PCT Filed: Sep. 17, 1994

[86] PCT No.: PCT/EP94/03116

§ 371 Date: Oct. 18, 1996

§ 102(e) Date: Oct. 18, 1996

[87] PCT Pub. No.: WO95/08547

PCT Pub. Date: Mar. 30, 1995

[30] Foreign Application Priority Data

Sep. 22, 1993 [DE] Germany ............... 43 32 203.4

[51] Int. Cl.⁶ ............... C07D 405/06; C07D 409/06; A61K 31/365

[52] U.S. Cl. ............... 514/460; 549/292; 549/13; 514/336; 514/397; 514/408; 514/444; 546/282.1; 548/335.5; 548/518

[58] Field of Search ............... 549/292, 13; 514/460, 514/444, 408, 336, 397; 546/282.1; 548/335.1, 518

[56] References Cited

PUBLICATIONS

Aminov et al, Chemical Abstracts, vol. 116, No. 12, Abstract No. 120, 411v, p. 20, 1992.

*Primary Examiner*—Zinna Northington Davis
*Attorney, Agent, or Firm*—Nikaido, Marmelstein, Murray & Oram LLP

[57] ABSTRACT

The invention concerns new bishipidine derivatives, processes for their production and pharmaceutical agents containing these compounds. The new methylene-bishispidine derivatives can be used for the prophylaxis and therapy of late diabetic damage as well as for the prophylaxis and therapy of atherosclerosis and arteriosclerosis.

11 Claims, No Drawings

BISHISPIDINE COMPOUNDS, PROCESSES FOR THEIR PRODUCTION AND PHARMACEUTICAL AGENTS CONTAINING THESE COMPOUNDS

This application is a 371 of PCT/EP94/03116 filed Sep. 17, 1994, published as WO95/08547, Mar. 30, 1995.

The present invention concerns methylene-bishispidine derivatives, processes for their production and pharmaceutical agents that contain these compounds.

The invention concerns methylene-bishispidine derivatives of the general formula I in which
A denotes hydrogen, $C_1$–$C_{16}$ alkyl, $C_3$–$C_6$ cycloalkyl, a group in which
$R_1$–$R_5$ simultaneously or independently of one another denote hydrogen, $C_1$–$C_6$ alkyl, hydroxy, $C_1$–$C_6$ acyloxy, $C_1$–$C_6$ alkoxy, benzyloxy, halogen, cyano, carboxy, amino, phenyl, alkylthio, carboxyalkyl, heteroalkyl or an ester group,
X is —$CR_6$=$CR_7$—, —$CR_8$=N—, —N=$CR_9$—, oxygen or sulphur,
Y is —$CR_6$=$CR_7$—, —$CR_{11}$=N—, $NR_{10}$, oxygen or sulphur
Z is =$CR_{11}$— or nitrogen
in which
$R_6$–$R_{11}$ independently of one another denote hydrogen, methyl, halogen or carboxy and
W denotes hydrogen, $C_1$–$C_4$ alkyl, optionally substituted by halogen, arylalkyl, carboxyl or carboxyl ester.
as well as physiologically tolerated salts or esters thereof.

The alkyl residues in the said alkyl, alkoxy, acyloxy, alkylthio, carboxyalkyl or heteroalkyl groups can be straight-chained or branched. A $C_1$–$C_6$ alkyl residue in the present invention denotes methyl, ethyl, propyl, isopropyl, butyl, isobutyl, t-butyl, pentyl or hexyl. Heteroalkyl denotes a $C_1$–$C_4$ alkyl residue substituted by nitrogen, oxygen or sulphur. Arylalkyl denotes a phenyl group which is optionally substituted by halogen, hydroxy or methyl and is linked by a $C_1$–$C_4$ alkyl residue. Carboxyalkyl is a carboxy group linked by a $C_1$–$C_4$ alkyl residue. Halogen denotes fluorine, chlorine, bromine or iodine, preferably chlorine.

It was surprisingly found that compounds of formula I have valuable pharmacological properties. In particular they inhibit the formation of AGE (Advanced Glycosylation Endproducts) whose significance for the development of late diabetic complications has been shown (A. Cerami, Trends Biochem. Sci. 11, 311 (1986)).

Thus the non-enzymatic glycosylation of plasma proteins can be stimulated in vitro by incubating them with glucose the reinjection of these proteins leads in vivo to typical late diabetic damage (H. Vlassara et al., Diabetes 41, Suppl. 1, 9A (1992)). AGE are involved in the thickening of the glomerular basal membrane, a process which is responsible for renal insufficiency and renal failure. The non-enzymatic glycosylation of crystallin, a protein of the eye lens, leads to changes in the tertiary structure and polymerization by oxidation of SH groups to disulfides resulting in diabetic cataract formation (V. Monnier, Clin. Endocrinol. Metab. 11, 431 (1982)). The cross-linking of proteins caused by the end products of non-enzymatic glycosylation reduces the solubility of collagen and is involved in the sclerosis of blood vessels (H. Rosenburg et al., Biochem. Biophys. Res. Commun. 91 498 (1979)). A further consequence is the capture of low density lipoproteins (M. Brownlee et al., Science 232, 1629 (1986)). The localization of these LDL proteins on the endothelium is a strong stimulus for atherosclerotic processes (D. Steinberg et al., J. Clin. Invest, 88, 1785 (1991); D. Leake, Current Opinion in Lipidology, 2, 301 (1991)).

Compounds of formula I are therefore suitable for the prophylaxis and treatment of late diabetic damage (e.g. retinopathy, nephropathy and neuropathy) as well as for the prophylaxis and therapy of atherosclerosis and arteriosclerosis.

Preferred compounds of the general formula I are compounds in which A denotes hydrogen, $C_1$–$C_6$-alkyl, $C_3$–$C_6$ cycloalkyl or a group in which $R_1$ and $R_5$ are hydrogen.

Particularly preferred compounds of the general formula I are those in which $R^3$ represents hydrogen, hydroxy, $C_1$–$C_4$ alkoxy, cyano, carboxy or halogen, $R^2$ and $R^4$ independently of one another and independently of $R^3$ denote hydrogen, hydroxy, $C_1$–$C_4$ alkyloxy or $C_1$–$C_4$ alkyl and $R^1$ and $R^5$ are hydrogen atoms.

Particularly preferred compounds of the general formula I are also those in which A denotes a group in which
X is —CH=CH—, NH, —CH=N, oxygen or sulphur,
Y is —CH=CH—, —CH=N— or sulphur and
Z is =CH— or nitrogen.

W in the general formula I is preferably hydrogen, $C_1$–$C_4$ alkyl or a carboxyl ester.

The compounds of the general formula I in which A and W have the meanings stated above are produced by condensing hispidine (II) with an aldehyde or a ketone of formula III

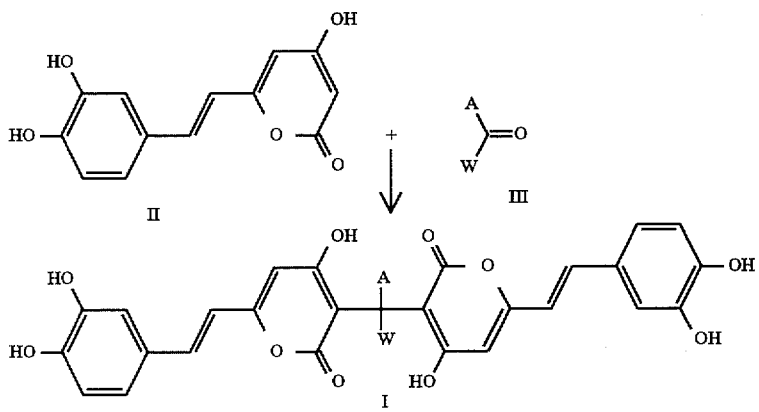

in this case A and W have the above-mentioned meanings. The reaction can be carried out by heating the two components in a polar organic solvent, preferably in protic solvents such as simple aliphatic alcohols, in particular methanol or ethanol, in the presence of catalytic amounts of a mineral acid such as hydrochloric acid or sulphuric acid. The reaction can also be carried out in a dipolar aprotic solvent such as dimethyl-formamide with addition of piperidinium acetate as a catalyst with azeotropic dehydration with toluene.

If the synthesized compounds of the general formula I are acidic or basic they can, if desired, be converted into physiologically tolerated salts and in the case of carboxylic acids it is possible to convert them into esters using physiologically acceptable alcohols. Pharmacologically acceptable inorganic or organic bases such as e.g. sodium hydroxide, potassium hydroxide, calcium hydroxide, methylene glucamine, morpholine or ethanolamine are suitable for the formation of salts from carboxylic acids of the general formula I. Acids which are suitable for forming salts with bases of the general formula I are for example hydrochloric acid, sulphuric acid, acetic acid, citric acid, maleic acid, fumaric acid and tartaric acid.

If the compounds of the general formula I contain a carboxyl function, esters of these carboxylic acids which come into consideration are those formed with lower monovalent alcohols (e.g. methanol or ethanol) or with polyvalent alcohols (such as e.g. glycerol).

The starting compound hispidine (II) used for the production of the compounds of formula I was discovered and structurally characterized almost simultaneously by R. L. Edwards et al. (isolation from Polyporus hispidus; J. chem. Soc. 1961, 4995) and A. Ueno et al. (isolation from Phaeolus schweinitzii"; Chem. Pharm. Bull. 12, 376 (1964)).

However, the amounts of hispidine which can be obtained by extraction from basidiomycetes are much too small to serve as the starting material for extensive syntheses and in-depth pharmacological investigations. Consequently there was an urgent need to develop an efficient chemical production process for hispidine.

A first but not very efficient hispidine synthesis was described in 1961 by Edwards et al. In this process 3,4-di(methoxymethoxy)benzaldehyde is reacted with 4-methoxymethoxy-6-methyl-2-pyrone in the presence of magnesium methanolate in methanol, the yield being only 2% hispidine since an extremely complex mixture of products is formed.

The reaction of 3,4-di(methoxymethoxy)benzaldehyde with 4-methoxy-6-methyl-2-pyrone in the presence of magnesium methanolate in methanol is stated as an alternative in the publication cited above. The subsequent alkaline saponification and acidic recyclization leads to such a complex reaction mixture that hispidine that is formed can only be isolated after acetylation as a tri-O-acetyl compound (5% yield). The isolation of the free hispidine then requires yet a further step involving heavy losses.

In both the processes described by Edwards et al the preparation of the starting materials used in addition requires the use of the highly carcinogenic chloromethyl ether which practically excludes an industrial application.

The subject matter of the present invention is thus a process which is based on the reaction of 3,4-dibenzyloxy-benzaldehyde IV with 4-benzyloxy-6-methyl-2-pyrone V in the presence of lithium diisopropylamide. The aldol compound VI formed can be debenzylated under very mild conditions by catalytic hydrogenation to form the tetrahydroxy compound VII. It is readily dehydrated to hispidine II with dilute acid. The process according to the invention has a very reproducible total yield (IV→II) of 30% and is thus considerably superior to the previously known methods for the preparation of hispidine.

For the production of pharmaceutical agents the compounds of the general formula I are mixed with suitable pharmaceutical carrier substances, aromatics, flavourings and dyes in a well-known manner and are for example formed into tablets or dragées or suspended or dissolved in water or oil such as e.g. olive oil with addition of corresponding auxiliary agents.

The methylene-bishispidine derivatives of the general formula I can be administered orally and parenterally in a liquid or solid form. Water is preferably used as the injection medium which contains the usual stabilizing agents, solubilizers and/or buffers for injection solutions. Such additives are for example tartrate or borate buffer, ethanol, dimethylsulfoxide, complexing agents (such as ethylenediaminetetraacetic acid), high molecular polymers (such as liquid polyethylene oxide) to regulate the viscosity or polyethylene derivatives of sorbitol anhydrides.

Solid carriers are e.g. starch, lactose, mannitol, methylcellulose, talcum, highly dispersed silicic acid, higher molecular polymers (such as polyethylene glycols). Preparations that are suitable for oral administration can if desired contain flavourings and sweeteners.

The administered dose depends on the age, state of health and weight of the recipient, the extent of the disease, the type of further treatments that are simultaneously carried out if desired and the type of the desired effect. The daily dose of the active compound is usually 0.1 to 50 mg/kg body weight.

0.5 to 40 and preferably 1.0 to 20 mg/kg/day in one or several administrations per day are usually effective in order to obtain the desired results.

Within the sense of the present invention the following compounds of formula I come into consideration in addition to the compounds mentioned in the examples and compounds derived by combination of all meanings of substituents mentioned in the claims, which can be present optionally as salts or esters.

1. 3,3'-(4-Hydroxybenzylidene)bis([6-[2-(3,4-dihydroxyphenyl)vinyl]-4-hydroxy-2H-pyran-2-one]
2. 3,3'-(2-Pyrrolylmethylene)bis[6-[2-(3,4-dihydroxyphenyl)vinyl]-4-hydroxy-2H-pyran-2-one]
3. 3,3'-(2-Phenylethylidene)bis[6-[2-(3,4-dihydroxyphenyl) vinyl]-4-hydroxy-2H-pyran-2 -one]
4. 3,3'-(4-Carboxybenzylidene)bis[6-[2-(3,4-dihydroxyphenyl)vinyl]-4-hydroxy-2H-pyran-2-one]

Examples of application
Synthesis of hispidine (II):
i) 4-Benzyloxy-6-methyl-2H-pyran-2-one (V)

124.4 g (0.900 mol) potassium carbonate and 63 ml (0.547 mol) benzyl chloride were added in succession to a solution of 56.7 g (0.450 mol) 4-hydroxy-6-methyl-2H-pyran-2-one and 1.0 g (0.004 mol) 18-crown-6 in 900 ml anhydrous dimethyl-formamide. It was stirred vigorously for 4.5 hours at an internal temperature of 70°–75° C. It was suction filtered and the residue was washed well with ethyl acetate. The combined filtrates were extensively evaporated in a vacuum and subsequently poured onto ice water. The aspirated precipitate was recrystallized from t-butylmethyl ether after drying. 69.0 g (71%) V, melting point 92°–93° C.

ii) 4-Benzyloxy-6-[2-(3,4-dibenzyloxyphenyl)-2-hydroxyethyl]-2H-pyran-2-one (VI)

A solution of 10.1 g (14.0 ml, 100 mmol) diisopropylamine in 150 ml tetrahydrofuran was mixed under nitrogen at −78° C. with 41.0 ml (95 mmol) butyllithium (2.3M in n-hexane). It was allowed to reach 0° C. for a short time and immediately cooled again to −78° C. After a dropwise addition of a solution of 19.0 g (88 mmol) 4-benzyloxy-6-methyl-2H-pyran-2-one (V) in 100 ml anhydrous tetrahydrofuran it was stirred for a further 45 min. at −78° C. and subsequently a solution of 12.8 g (40 mmol) 3,4-dibenzyloxy-benzaldehyde (IV) in 150 ml anhydrous tetrahydro-furan was added dropwise. The internal temperature was gradually increased to −30° C. and it was admixed with an excess of saturated ammonium chloride solution. After acidifying with 6n HCl it was extracted with ethyl acetate, the combined organic phases were dried and evaporated. Purification of the residue by means of flash chromatography on silica gel (mobile solvent: ethyl acetate/heptane 1:2) yielded 14.4 g (68%) VI, melting point 109°–110° C. (ether).

iii) 4-Hydroxy-6-[2-(3,4-dihydroxyphenyl)-2-hydroxyethyl]-2H-pyran-2-one (VII)

35.6 g (66.6 mmol) 4-benzyloxy-6-[2-[3,4-dibenzyloxyphenyl)-2-hydroxy-ethyl)]-2H-pyran-2-one (VI) was hydrogenated for 6 hours at room temperature under a hydrogen pressure of 44 mbar in 1200 ml ethanol using 10 g W2 Raney nickel. After taking up 4.4 l hydrogen the catalyst was removed by suction filtration and it was rewashed several times with tetrahydrofuran. The evaporated filtrates yielded 12.2 g (70%) VII after triturating with ether, melting point 153° C. (decomp.).

iv) 6-[2-(3,4-Dihydroxyphenyl)vinyl]-4-hydroxy-2H-pyran-2-one (hispidine), (II)

2 ml 3N HCl was added to a suspension of 8.0 g (30 mmol) 4-hydroxy-6-[2-(3,4-dihydroxyphenyl)-2-hydroxyethyl]-2H-pyran-2-one VII and 300 ml tetrahydrofuran. The resulting clear solution was heated for 2–3 hours under reflux until it was no longer possible to detect starting material. (TLC control, mobile solvent: toluene/ethyl formate/methanol 5:4:1, 0.5% formic acid). After drying over sodium sulphate the solution was strongly evaporated (residual volume ca. 50 ml) and it was crystallized by admixing with ether. Yield 4.7 g (63%) hispidine II, melting point 232°–234° C. (decomp.) or melting point 253° C. (decomp; bunch of needles from toluene/ethyl formate).

Synthesis of methylene-bishispidine derivatives of the general formula I:

EXAMPLE 1

3,3'-(4-Chlorobenzylidene)bis[6-[2-(3,4-dihydroxyphenyl) vinyl]-4-hydroxy-2H-pyran-2-one]

4.9 g (0.02 mol) hispidine was added to a solution of 7.0 g (0.05 mol) 4-chlorobenzaldehyde in 100 ml methanol and it was subsequently admixed with 2.0 ml hydrochloric acid. The mixture was stirred at 50° C. until the reaction was completed (progress monitored by TLC, mobile solvent: toluene/ethyl formate/formic acid 5:4:1). The reaction mixture was stirred into 500 ml water and the brown precipitate was aspirated (crude yield 6.1 g). For the purification it was precipitated from ethyl acetate/heptane. 3.1 g (50%), melting point 193° C. (decomp.).

EXAMPLE 2

3,3'-(4-Methylenebenzylidene)bis[6-[2-(3,4-dihydroxyphenyl)vinyl]-4-hydroxy-2H-pyran-2-one]

Analogously to example 1 the compound obtained from hispidine and 4-methylbenzaldehyde was stirred with ether after purification of the aspirated crude product by flash chromatography on silica gel (mobile solvent: toluene/dioxane/glacial acetic acid 72:20:8). Yield 43%, melting point 192° C. (decomp.).

EXAMPLE 3

3,3'-(3-Hydroxy-4-methoxybenzylidene)bis[6-[2-(3,4-dihydroxyphenyl)vinyl]-4-hydroxy-2H-pyran-2-one] (3)

Analogously to example 2 from hispidine and 3-hydroxy-4-methoxybenzaldehyde. Mobile solvent: toluene/ethyl formate/methanol 5:4:1, 0.5% formic acid. Yield: 36%, melting point 181° C. (decomp.).

EXAMPLE 4

3,3'-(4-Hydroxy-3,5-(bis-1,1-dimethylethyl) benzylidene] bis[6-[2-(3,4-dihydroxyphenyl)vinyl]-4-hydroxy-2H-pyran-2-one] (4)

Analogously to example 2 from hispidine and 4-hydroxy-3,5-(bis-1,1-di-methylethyl)-benzaldehyde. Mobile solvent: toluene/dioxane/glacial acetic acid 72:20:8) Yield: 40%, melting point 148° C. (decomp.).

EXAMPLE 5

3,3'-(4-Methoxybenzylidene)bis[6-[2-(3,4-dihydroxyphenyl)vinyl-4-hydroxy-2H-pyran-2-one] (5)

Analogously to example 2 from hispidine and 4-methoxybenzaldehyde. Mobile solvent toluene/ethyl formate/methanol 5:4:1, 1% formic acid. Yield 28%, melting point 167° C. (decomp.).

EXAMPLE 6

3,3'-(3,4-Dimethoxybenzylidene)bis[6-[2-(3,4-dihydroxyphenyl)vinyl-4-hydroxy-2H-pyran-2-one]

Analogously to example 2 from hispidine and 3,4-dimethoxy-benzaldehyde. Mobile solvent toluene/ethyl formate/methanol 5:4:1, 0.5% formic acid. Yield 32%, melting point 177° C. (decomp.).

EXAMPLE 7
3,3'-(3,4-Dihydroxybenzylidene)bis[6-[2-(3,4-dihydroxyphenyl)vinyl-4-hydroxy-2H-pyran-2-one] (7)

Analogously to example 2 from hispidine and 3,4-dihydroxy-benzaldehyde. Mobile solvent toluene/ethyl formate/methanol 5:4:1, 1% formic acid. Yield 41%, melting point 238° C. (decomp.).

EXAMPLE 8
3,3'-[4-Cyanobenzylidene)bis[6-[2-(3,4-dihydroxyphenyl)vinyl-4-hydroxy-2H-pyran-2-one] (8)

Analogously to example 1 from hispidine and 4-cyanobenz-aldehyde. Recrystallized from ethyl acetate/heptane. Yield 41%, melting point 198° C. (decomp.).

EXAMPLE 9
3,3'-Benzylidenebis[6-[2-(3,4-dihydroxyphenyl)vinyl-4-hydroxy-2H-pyran-2-one] (9)

Analogously to example 2 from hispidine and benzaldehyde. Mobile solvent toluene/ethyl formate/methanol 5:4:1, 0.5% formic acid. Yield 33%, melting point 163° C. (decomp.).

EXAMPLE 10
3,3'-Methylenebis[6-[2-(3,4-dihydroxyphenyl)vinyl-4-hydroxy-2H-pyran-2-one] (10)

Analogously to example 2 from 1.00 g (4.00 mmol) hispidine and 15 ml (0.2 mol) 35% formalin solution. Re-precipitated from tetrahydrofuran/isohexane. Yield 28%, melting point 290° C. (decomp.).

EXAMPLE 11
3,3'-(2-Thienylmethylene)bis[6-[2-(3,4-dihydroxyphenyl)vinyl-4-hydroxy-2H-pyran-2-one] (11)

Analogously to example 2 from hispidine and thiophene-2-aldehyde. Mobile solvent toluene/ethyl formate/methanol 5:4:1, 0.5% formic acid. Yield 31%, melting point >300° C.

EXAMPLE 12
3,3'-(2-Pyridylmethylene)bis[6-[2-(3,4-dihydroxyphenyl)vinyl-4-hydroxy-2H-pyran-2-one]hydrochloride (12)

Analogously to example 1 from hispidine and pyridine-2-aldehyde. The aspirated precipitate was intensively washed with ethyl acetate. Yield 55%, melting point 228° C. (decomp.).

EXAMPLE 13
3,3'-(3,4,5-Trimethoxybenzylidene)bis[6-[2-(3,4-dihydroxyphenyl)vinyl-4-hydroxy-2H-pyran-2-one]

Analogously to example 2 from hispidine and 3,4,5-trimethoxybenzaldehyde. Mobile solvent: toluene/ethyl formate/methanol 5:4:1, 0.5% formic acid. Yield 30%, melting point 208° C. (decomp.).

EXAMPLE 14
3,3'-(3-Thienylmethylene)bis[6-[2-(3,4-dihydroxyphenyl)vinyl-4-hydroxy-2H-pyran-2-one] (14)

Analogously to example 2 from hispidine and thiophene-3-aldehyde. Mobile solvent: toluene/ethyl formate/methanol 5:4:1, 0.5% formic acid. Yield 35%, melting point 243° C. (decomp.).

EXAMPLE 15
3,3'-(1-Hexylidene)bis[6-[2-(3,4-dihydroxyphenyl)vinyl-4-hydroxy-2H-pyran-2-one]

Analogously to example 2 from 1.00 g (4.00 mmol) hispidine and 9.6 ml (80 mmol) hexanal. Mobile solvent: toluene/ethyl formate/methanol 5:4:1, 0.5% formic acid. Yield 45%, melting point 109° C. (decomp.).

EXAMPLE 16
3,3'-(2-Imidazolylmethylene)bis[6-[2-(3,4-dihydroxyphenyl)vinyl-4-hydroxy-2H-pyran-2-one] hydrochloride (16)

Analogously to example 2 from hispidine and imidazole-2-aldehyde. Mobile solvent: toluene/ethyl formate/methanol 5:4:1, 0.5% formic acid. Yield 4%, melting point 147° C. (decomp.).

EXAMPLE 17
3,3'-(4-Bromobenzylidene)bis[6-[2-(3,4-dihydroxyphenyl)vinyl-4-hydroxy-2H-pyran-2-one] (17)

Analogously to example 2 from hispidine and 4-bromobenz-aldehyde. Mobile solvent: toluene/ethyl formate/methanol 5:4:1, 0.5% formic acid. Yield 27%, melting point 228° C. (decomp.).

EXAMPLE 18
3,3'-(4-Benzyloxybenzylidene)bis[6-[2-(3,4-dihydroxyphenyl)vinyl-4-hydroxy-2H-pyran-2-one] (18)

Analogously to example 2 from hispidine and 4-benzyloxy-benzaldehyde. Mobile solvent: toluene/ethyl formate/methanol 5:4:1, 0.5% formic acid. Yield 11%, melting point 180° C. (decomp.).

EXAMPLE 19
3,3'-Methoxycarbonylmethylenebis[6-[2-(3,4-dihydroxyphenyl)vinyl-4-hydroxy-2H-pyran-2-one] (19)

Analogously to example 2 from hispidine and glyoxylic acid. Mobile solvent: toluene/ethyl formate/methanol 5:4:1, 0.5% formic acid. Yield 18%, melting point 203° C. (decomp.).

EXAMPLE 20
3,3'-(Cyclohexylmethylene)bis[6-[2-(3,4-dihydroxyphenyl)vinyl-4-hydroxy-2H-pyran-2-one] (20)

Analogously to example 2 from 1.00 g (4.00 mmol) hispidine and 6.7 g (60 mmol) cyclohexanaldehyde. purification of the aspirated precipitate by flash chromatography on silica gel (mobile solvent: toluene/ethyl formate/methanol 5:4:1, 0.5% formic acid. Yield 36%, melting point 154° C. (decomp.).

DESCRIPTION OF THE EXPERIMENT

Test for the inhibitory activity on the formation of AGE

Lysozyme is dissolved at a final concentration of 20 mg/ml in 100 mmol/l potassium phosphate buffer, pH 7.4. 5 mmol/l sodium azide is added as a preservative. The formation of AGE is initiated by the addition of 200 mmol/l glucose or xylose. Test substances or the reference substance aminoguanidine are added at different concentrations in order to quantify an inhibitory activity on AGE formation. Solvent controls as well as control mixes are also run in the presence of 200 mmol/l sorbitol or xylite for correction purposes. The incubation period of the reaction mixtures is between 24 and 120 hours depending on the sugar used and is selected in such a way that mainly dimers are formed and other higher molecular oligomerization products are formed only to a slight extent.

The samples are prepared and SDS gel electrophoresis is carried out according to literature references. Summarized briefly the samples are diluted with the 4-fold amount of sample buffer (50 mmol/l Tris* acetate, pH 7.5, 1% SDS, 5 mmol/l dithiothreitol) and heated for 3 minutes to 95° C. Aliquots are applied to 8–18% gradient-SDS gels. In order to determine the molecular weight molecular weight markers are also used in the range 14–340 kD. The separation according to molecular weight is achieved under the following operating conditions: voltage: 600 V, current intensity: 50 mA, power: 30 W, run period: ~60 minutes.

After the gel electrophoresis the gels are fixed according to standard methods and stained with Coomassie Blue. After destaining overnight and drying, the gels are measured densitometrically (Pharmacia Ultra Scan XL using GelScan XL software).

In order to determine the threshold concentration and the $IC_{50}$ values of the AGE-inhibitory action of the test substances, the dimer formation is plotted semi-logarithmically against the test concentration of the substance and the above-mentioned parameters are calculated.

TABLE

| Compound Example No. | Threshold concentration [μmol/l] | $IC_{50}$ [μmol/l] |
|---|---|---|
| 1 | >1 | 4 |
| 3 | >1 | 2 |
| 4 | >1 | 2 |
| 5 | >1 | 2 |
| 6 | >1 | 5 |
| 7 | 2 | 4 |
| 8 | 10 | 22 |
| aminoguanidine | 500 | 4500 |

We claim:

1. A methylene-bishispidine compound of the formula

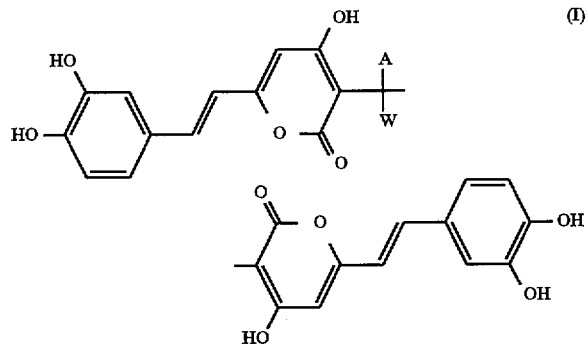

(I)

wherein

A is hydrogen, $C_1-C_{16}$ alkyl, $C_3-C_6$ cycloalkyl or a group of the formula

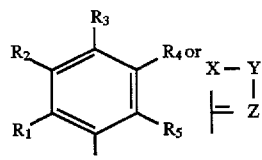

wherein $R_1-R_5$ are independently hydrogen, $C_1-C_6$ alkyl, hydroxy, $C_1-C_6$ acyloxy, $C_1-C_6$ alkoxy, benzyloxy, halogen, cyano, carboxy, amino, phenyl, alkylthio, carboxy-$C_1-C_4$-alkyl, $C_1-C_4$ alkyl substituted by nitrogen, oxygen or sulphur, or an ester of a $C_1-C_6$ carboxylic acid with a $C_1-C_4$ alcohol or a $C_1-C_4$ polyol;

X is —$CR_6$=$CR_7$—, —$CR_8$=N—,
—N=$CR_9$—, oxygen or sulphur,

Y is —$CR_6$=$CR_7$—, —$CR_{11}$=N—,
—$NR_{10}$—, oxygen or sulphur,

Z is =$CR_{11}$— or nitrogen, wherein $R_6-R_{11}$ are independently hydrogen, methyl, halogen or carboxy; and W is hydrogen, $C_1-C_4$ alkyl which is unsubstituted or substituted by halogen, phenyl-$C_1-C_4$-alkyl wherein the phenyl ring is unsubstituted or substituted by halogen, hydroxy or methyl, carboxyl or an ester of a $C_1-C_6$ carboxylic acid with a $C_1-C_4$ alcohol or a $C_1-C_4$ polyol; or a physiologically tolerated salt or ester thereof.

2. A methylene-bishispidine compound of claim 1 wherein

A is hydrogen, $C_1-C_6$ alkyl, $C_3-C_5$ cycloalkyl, or a group of the formula

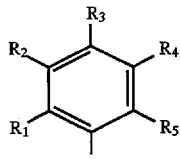

wherein $R_1$ and $R_5$ are hydrogen.

3. A methylene-bishispidine compound of claim 2, wherein $R_3$ is hydrogen, hydroxy, $C_1-C_4$ alkoxy, cyano, carboxy or halogen, and $R_2$ and $R_4$ are independently hydrogen, hydroxy, $C_1-C_4$ alkoxy or $C_1-C_4$ alkyl.

4. A methylene-bishispidine compound as claimed in claim 1, wherein A is a group of the formula

wherein

X is —CH=CH—, —NH—, —CH=N—, oxygen or sulphur;

Y is —CH=CH—, —CH=N— or sulphur; and

Z is =CH— or nitrogen.

5. A methylene-bishispidine compound of claim 1, wherein W is hydrogen, $C_1-C_4$ alkyl or a carboxyl ester.

6. A methylene-bishispidine compound of claim 1, wherein said derivative is:

3-3'-(4-Hydroxybenzylidene)bis(6-[2-(3,4-dihydroxyphenyl)vinyl]-4-hydroxy-2H-pyran-2-one], 3,3'-(2-Pyrrolylmethylene)bis [6-[2-(3,4-dihydroxyphenyl)vinyl]-4-hydroxy-2H-pyran-2-one], 3,3'-(2-Phenylethylidene)bis [6-[2-(3,4-dihydroxyphenyl)vinyl]-4-hydroxy-2H-pyran-one], 3,3'-(4-Carboxybenzylidene)bis[6-[2-(3,4-dihydroxyphenyl)vinyl]-4-hydroxy-2H-pyran-one], 3,3'-(4-Chlorobenzylidene)bis [6-[2-(3,4-dihydroxyphenyl)vinyl]-4-hydroxy-2H-pyran-2-one], 3,3'-(Methoxybenzylidene)bis [6-[2-(3,4-dihydroxyphenyl)vinyl]-4-hydroxy-2H-pyran-2-one], 3,3'-(3-Hydroxy-4-methoxybenzylidene)bis[6-[2-(3,4-dihydroxyphenyl)vinyl]-4-hydroxy-2H-pyran-2-one], 3,3'-(4-Hydroxy-3,5-(bis-1,1-dimethylethyl) benzylidene] bis[6-[2-(3,4-dihydroxyphenyl)vinyl]-4-hydroxy-2H-pyran-2-one], 3,3'-(4-Methoxybenzylidene)bis[6-[2-(3,4-dihydroxphenyl)vinyl-4-hydroxy-2H-pyran-2-one], 3,3'-(3,4-Dimethoxybenzylidene)bis[6-[2-(3,4-dihydroxphenyl)vinyl]-4-hydroxy-2H-pyran-2-one], 3,3'-(3,4-Dimethoxybenzylidene)bis[6-[2-(3,4-dihydroxphenyl)vinyl]-4-hydroxy-2H-pyran-2-one], 3,3'-(4-Cyanobenzylidene)bis[6-[2-(3,4-dihydroxyphenyl)vinyl-4-hydroxy-2H-pyran-2-one], 3,3'-Benzylidenebis[6-[2-(3,4-dihydroxphenyl)vinyl-4-hydroxy-2H-pyran-2-one], 3,3'-Methylenebis[6-[2-(3,4-dihydroxphenyl)vinyl-4-hydroxy-2H-pyran-2-one], 3,3'-(2-Thienylmethylene)bis[6-[2-(3,4-dihydroxphenyl)vinyl-4-hydroxy-2H-pyran-2-one], 3,3'-(2-Pyridylmethylene)bis[6-[2-(3,4-dihydroxphenyl)vinyl-4-hydroxy-2H-pyran-2-one]hydrochloride, 3,3'-(3,4,5,-Trimethoxybenzylidene)bis[6-[2-(3,4-dihydroxphenyl)vinyl-4-hydroxy-2H-pyran-2-one], 3,3'-(3-Thienylmethylene)bis[6-[2-(3,4-dihydroxphenyl)vinyl-4-hydroxy-2H-pyran-2-one], 3,3'-(1-Hexylidene)bis[6-[2-(3,4-dihydroxphenyl)vinyl-4-hydroxy-2H-pyran-2-one], 3,3'-(2-Imidazolylmethylene)bis[6-[2-(3,4-dihydroxphenyl)vinyl-4-hydroxy-2H-pyran-2-one]hydrochloride, 3,3'-(4-Bromobenzylidenebis[6-[2-(3,4-dihydroxphenyl)vinyl-4-hydroxy-2H-pyran-2-one], 3,3'-(4-Benzyloxybenzylidene)bis[6-[2-(3,4-dihydroxphenyl)vinyl-4-hydroxy -2H-pyran-2-one], 3,3'-Methoxycarbonylmethylenebis[6-[2-(3,4-dihydroxphenyl)vinyl-4-hydroxy-2H-pyran-2-one], or 3,3'-(Cyclohexylmethylene)bis[6-[2-(3,4-dihydroxphenyl)vinyl-4-hydroxy-2H-pyran-2-one].

7. A pharmaceutical composition suitable for the inhibition of the formation of Advanced Glycosylation Endproducts comprising an effective amount of a methylene-bishispidine compound of claim 1 and a pharmaceutically acceptable carrier therefor.

8. A method for the treatment of late diabetic damage, atherosclerosis or arteriosclerosis in a patient in need of such treatment, comprising administering to the patient an effective amount of a methylene-bishispidine compound of claim 1.

9. A method of inhibiting the formation of Advanced Glycosylation Endproducts (AGE) in a patient in need of such inhibition, comprising administering to the patient an AGE-inhibiting effective amount of a methylene-bishispidine compound of claim 1.

10. A process for producing a methylene-bishispidine derivative of claim 1, comprising reacting hispidine of the formula

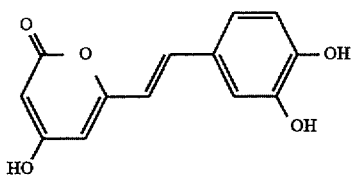

(II)

with an aldehyde or ketone of the formula

(III)

wherein A and W are defined in claim 1, with heating in a polar organic solvent in the presence of a catalytic amount of a mineral acid or in a dipolar aprotic solvent in the presence of a catalytic amount of piperidinium acetate under azeotropic dehydration.

11. A process according to claim 10, wherein the hispidine is produced by reacting 3,4-dibenzyloxybenzaldehyde of the formula:

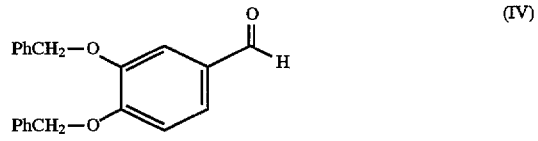

(IV)

with 4-benzyloxy-6-methyl-2H-pyran-2-one of the formula:

(V)

in the presence of lithium diisopropylamide to form an aldol compound of the formula:

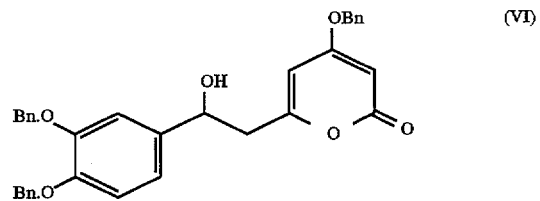

(VI)

thereafter debenzylating the aldol compound to form a tetrahydroxy compound of the formula:

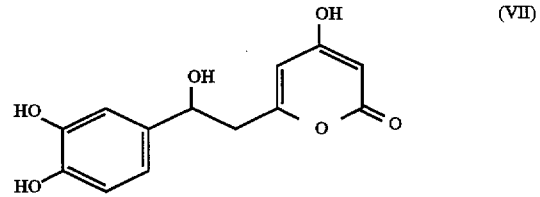

(VII)

and thereafter dehydrating the tetrahydroxy compound to form hispidine.

* * * * *